US012779221B2

(12) United States Patent
Grossoehmichen et al.

(10) Patent No.: US 12,779,221 B2
(45) Date of Patent: Nov. 3, 2026

(54) COCHLEAR IMPLANTS INCLUDING VIBRATION DRIVEN ELECTRODE ARRAYS AND ASSOCIATED METHODS

(71) Applicant: ADVANCED BIONICS, LLC, Valencia, CA (US)

(72) Inventors: Martin Grossoehmichen, Nienhagen (DE); Stephan Geiger, Hannover (DE)

(73) Assignee: Advanced Bionics, LLC, Valencia, CA (US)

( * ) Notice: Subject to any disclaimer, the term of this patent is extended or adjusted under 35 U.S.C. 154(b) by 291 days.

(21) Appl. No.: 18/451,445

(22) Filed: Aug. 17, 2023

(65) Prior Publication Data

US 2025/0058110 A1 Feb. 20, 2025

(51) Int. Cl.
*A61N 1/36* (2006.01)
*A61N 1/05* (2006.01)

(52) U.S. Cl.
CPC ....... *A61N 1/36038* (2017.08); *A61N 1/0541* (2013.01)

(58) Field of Classification Search
None
See application file for complete search history.

(56) References Cited

U.S. PATENT DOCUMENTS 5,653,742 A * 8/1997 Parker ..................... A61D 7/00 607/116
5,824,022 A 10/1998 Zilberman et al.
9,017,136 B2 4/2015 Norman et al.
10,022,534 B2 7/2018 Hüttenbrink et al.
10,118,028 B2 11/2018 Smith et al.
2010/0048983 A1* 2/2010 Ball ..................... H04R 25/606 607/57
2010/0268312 A1* 10/2010 Wallace ............... A61N 1/0541 607/116
2011/0202120 A1* 8/2011 Ball ..................... A61N 1/0541 607/137
2012/0109274 A1* 5/2012 Simaan ................ A61N 1/0541 607/137
2012/0184804 A1* 7/2012 Huttenbrink ......... A61N 1/0541 600/25
2012/0197265 A1* 8/2012 Sieber .................. A61N 1/0541 606/129
2016/0051819 A1* 2/2016 Koka .................. A61N 1/0541 607/57

FOREIGN PATENT DOCUMENTS

WO WO 2018/031025 A1 2/2018
WO WO 2018/102695 A1 6/2018

* cited by examiner

*Primary Examiner* — Erica S Lee
(74) *Attorney, Agent, or Firm* — Henricks Slavin LLP

(57) ABSTRACT

A cochlear implant including a housing, an antenna within the housing, a stimulation processor within the housing operably connected to the antenna and an electrode array, operably connected to the stimulation processor, including a flexible array body, a plurality of electrically conductive contacts on the flexible array body, a plurality of flexible projections that extend outwardly from the flexible array body, and a vibration device.

17 Claims, 6 Drawing Sheets

COCHLEAR IMPLANTS INCLUDING VIBRATION DRIVEN ELECTRODE ARRAYS AND ASSOCIATED METHODS

BACKGROUND

1. Field

The present disclosure relates generally to the implantable portion of implantable cochlear stimulation (or "ICS") systems and, in particular, to electrode arrays.

2. Description of the Related Art

Referring to FIGS. 1 and 2, the cochlea 10 is a hollow, helically coiled, tubular bone (similar to a nautilus shell) that is divided into the scala vestibuli 12, the scala tympani 14 and the scala media 16 by the Reissner's membrane 18 and the basilar membrane 20. The cochlea 10, which typically includes approximately two and a half helical turns, is filled with a fluid that moves in response to the vibrations coming from the middle ear. As the fluid moves, a tectorial membrane 22 and thousands of hair cells 24 are set in motion. The hair cells 24 convert that motion to electrical signals that are communicated via neurotransmitters to the auditory nerve 26, and transformed into electrical impulses known as action potentials, which are propagated to structures in the brainstem for further processing. Many profoundly deaf people have sensorineural hearing loss that can arise from the absence or the destruction of the hair cells 24 in the cochlea 10. Other aspects of the cochlea 10 illustrated in FIGS. 1 and 2 include the medial wall 28, the lateral wall 30 and the modiolus 32.

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths, rates, and/or amplitudes, and transmitted to an implanted receiver circuit of the ICS system. The implanted receiver circuit is connected to an implantable lead with an electrode array that is inserted into the cochlea of the inner ear, and electrical stimulation current is applied to varying electrode combinations to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Advanced Bionics™ Harmony™ BTE sound processor, the Advanced Bionics™ Naida™ BTE sound processor and the Advanced Bionics™ Neptune™ body worn sound processor.

As alluded to above, some ICS systems include an implantable cochlear stimulator (or "cochlear implant") having a lead with an electrode array, a sound processor unit (e.g., a body worn processor or behind-the-ear processor) that communicates with the cochlear implant, and a microphone that is part of, or is in communication with, the sound processor unit. The cochlear implant electrode array includes a flexible body formed from a resilient material and a plurality of electrically conductive contacts (e.g., sixteen platinum contacts) spaced along a surface of the flexible body. The cross-sectional size of the flexible body may taper from the base (or "basal") end to the tip (or "apical") end. The contacts of the array are connected to lead wires that extend through the flexible body. Exemplary cochlear leads are illustrated in WO2018/031025A1 and WO2018/102695A1, which are incorporated herein by reference in their entireties.

The precise insertion and accurate placement of the electrode array within the cochlea are important aspects of ICS therapy in that they reduce the likelihood of tissue damage and increase the likelihood of effective electrical stimulation. For example, the electrode array should stay within the scala tympani of the cochlea and be oriented correctly. In those instances where the patient has residual hearing, which is important to preserve so that the patient can benefit from combined electro-acoustic hearing assistance, trauma to the intracochlear structures during electrode array insertion should be minimized.

The present inventors have determined that conventional electrode array insertion techniques can result in less than optimal insertion and placement of the electrode array and are susceptible to improvement. Flexible electrode arrays are pushed by a surgeon into the cochlea from the basal end of the array and, as a result, the surgeon has limited and indirect control over the movement and position of the tip end. Given that the cochlea is a helical structure that varies considerably in size and morphology from patient to patient, that the electrode array is flexible, and that surgeon must rely on tactile feedback after the tip end has passed the first turn of the cochlea, pushing the electrode array from the basal end with limited control can result in damage to and/or misplacement of the electrode array as well as unwanted trauma to the cochlea. Misplacement of the electrode array reduces the effectiveness of the cochlear implant and may necessitate a revision surgery to more accurately place the electrode array. Misplacement of the electrode array as it is moving in the apical direction can result in scraping of the cochlea, folding of the electrode array, buckling of the electrode array, and breaching of the basilar membrane. The associated damage to the inner ear can result in a reduction in (or loss of) the residual hearing that was present prior to the cochlear implant insertion, thereby reducing the likelihood that the cochlear implant recipient will be able to benefit from combined electro-acoustic hearing assistance.

SUMMARY

A cochlear implant in accordance with at least one of the present inventions comprises a housing, an antenna within the housing, a stimulation processor within the housing operably connected to the antenna and an electrode array, operably connected to the stimulation processor, including a flexible array body, a plurality of electrically conductive contacts on the flexible array body, a plurality of flexible projections that extend outwardly from the flexible array body, and a vibration device.

A method in accordance with at least one of the present inventions comprises moving a cochlear implant electrode array, including a flexible array body, a plurality of electrically conductive contacts on the flexible array body, and a plurality of flexible projections that extend outwardly from the flexible array body, in an apical direction by vibrating the flexible body with a vibration device.

There are a number of advantages associated with such apparatus and methods. By way of example, but not limitation, the present electrode arrays are capable of moving through the narrow passages and curves of the cochlea without pushing by the surgeon, and will stop moving if the resistance is too great, thereby preventing trauma to the cochlea and damage to the electrode array. The present electrode arrays may also be moved through the cochlea solely by vibration-based driving force or by a combination of vibration-based driving force and force applied by the surgeon. The configurations of the flexible projections may be such that, once inserted, the flexible projections prevent unintended post-surgical electrode array movement in the basal direction while also allowing for a surgeon to move the electrode array in the basal direction, if necessary, without cochlear trauma.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

Figure 2:
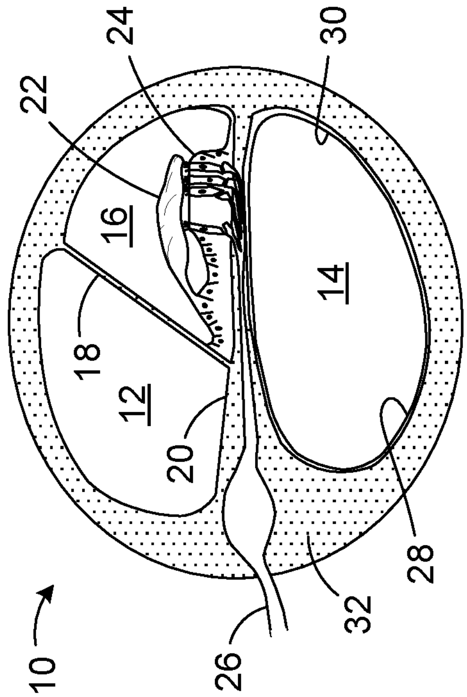
FIG. 2 is another section view of the cochlea.
Figure 1:
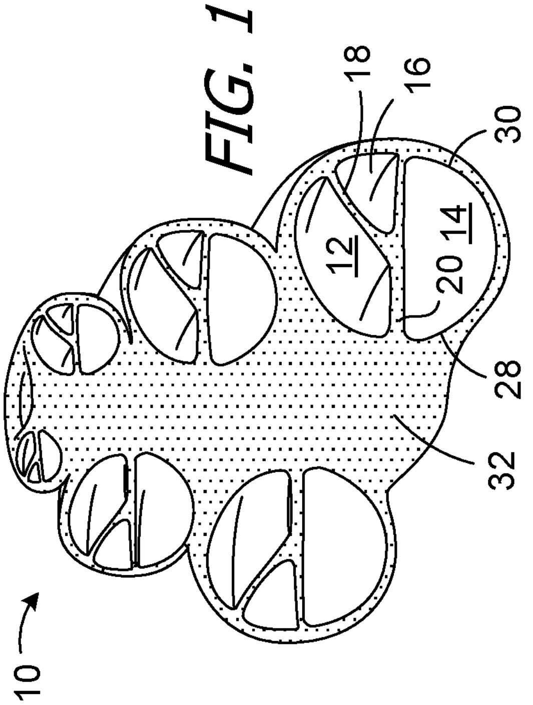
FIG. 1 is a section view of a cochlea.
Figures 3, 4:
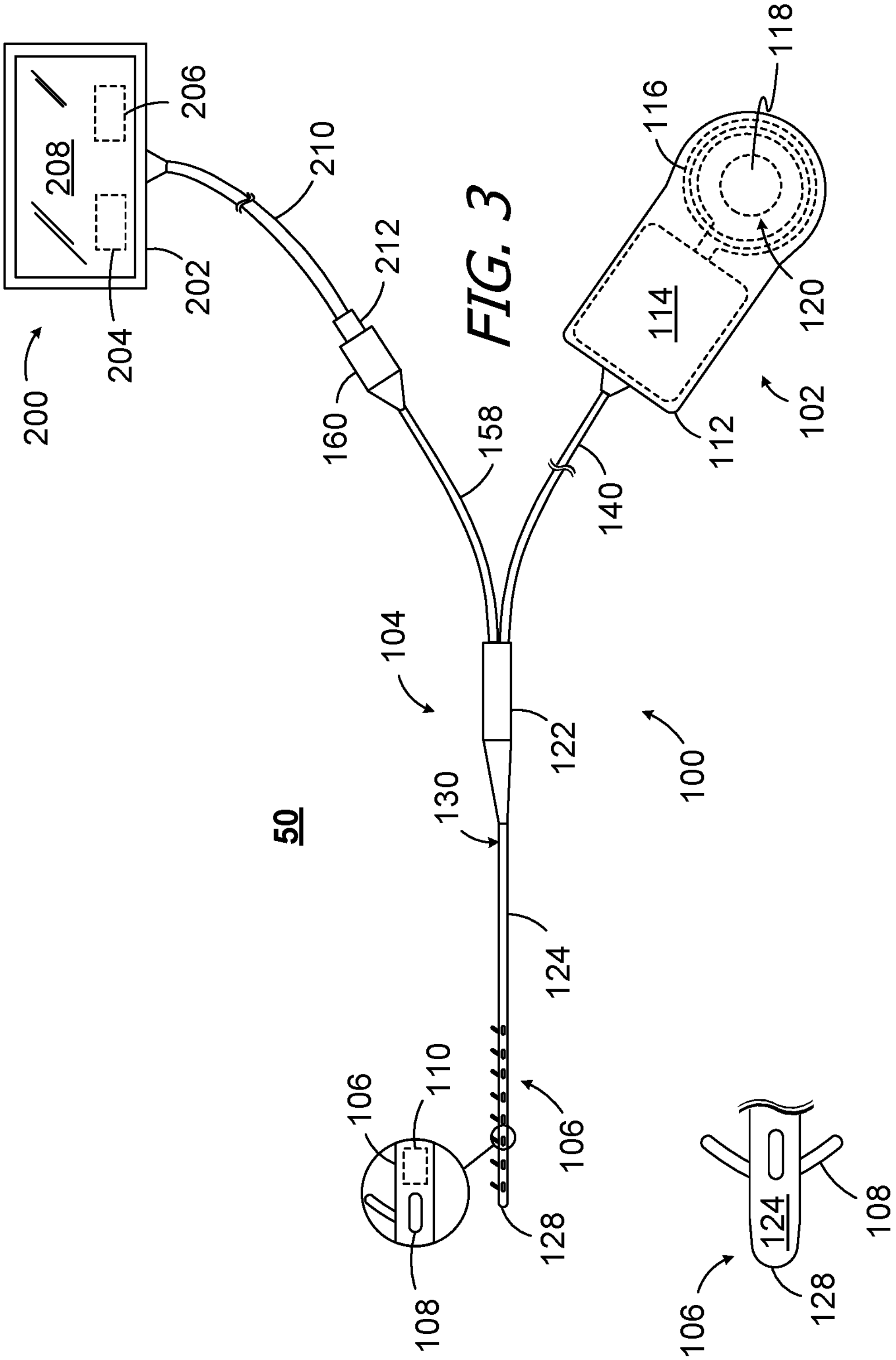
FIG. 3 is a view of an implantable cochlear stimulator and a vibration energy source in accordance with one embodiment of a present invention.
FIG. 4 is a top view of a portion of the electrode array illustrated in FIG. 3.
Figure 5:
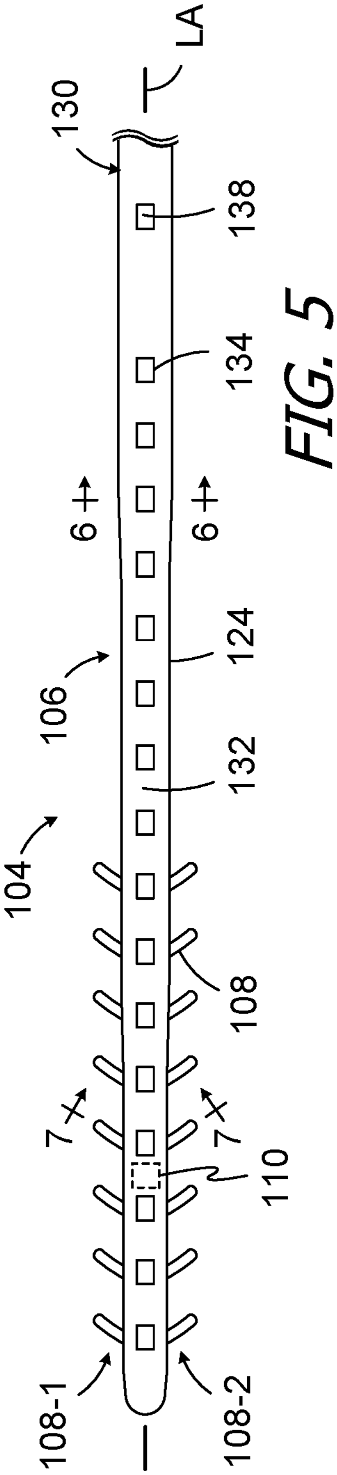
FIG. 5 is a bottom view of a portion of the electrode array illustrated in FIG. 3.
Figure 6:
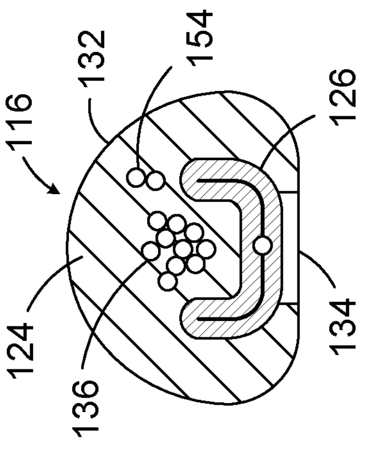
FIG. 6 is a section view taken along line 6-6 in FIG. 5.
Figure 7:
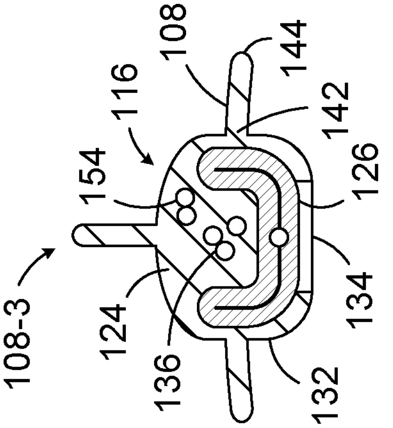
FIG. 7 is a section view taken along line 7-7 in FIG. 5.
Figure 8:
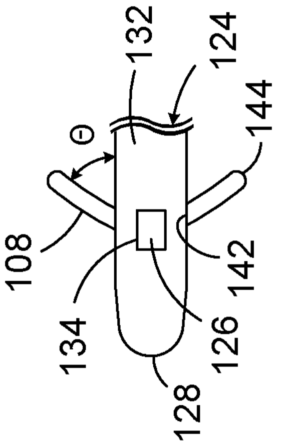
FIG. 8 is a bottom view of a portion of the electrode array illustrated in FIG. 3.

As illustrated for example in FIGS. 3 and 4, a system 50 in accordance with one embodiment of a present invention includes an implantable cochlear stimulator (or "cochlear implant") 100, with a stimulation assembly 102 and a cochlear lead 104 that has an electrode array 106, and a power supply and control device 200 that is operably connected to the electrode array. The electrode array 106 includes a plurality of flexible projections 108 and a vibration device 110. As is discussed in greater detail below, actuation of the vibration device 110 by the power supply and control device 200 causes vibration of the electrode array 106 that, in combination with the orientation of the projections 108, results in movement of the electrode array 106 in the apical (or "forward") direction as is discussed in greater detail below with reference to FIGS. 15 and 16.

Referring first to the exemplary cochlear implant 100, the stimulation assembly 102 includes a flexible housing 112 formed from a silicone elastomer or other suitable material, a processor assembly 114, an antenna 116 that may be used to receive data and power by way of an external antenna that is associated with, for example, a sound processor unit, and a positioning magnet 118 located within a magnet pocket 120. The magnet 118 is used to maintain the position of a sound processor headpiece over the antenna 116. The cochlear implant may, in some instances, be configured in a manner that facilitates magnet removal and replacement. Here, the housing 112 may be provided with a magnet aperture (not shown) that extends from the magnet pocket 120 to the exterior of the housing.

In addition to the electrode array 106, the exemplary cochlear lead 104 includes, in at least some instances, a wing 122 that functions as a handle for the surgeon during the implantation surgery. Other types of handles may also be employed. Referring also to FIGS. 5-8, the exemplary electrode array 106 has a flexible body 124 and a plurality of electrically conductive contacts 126 (e.g., sixteen contacts) spaced along the flexible body between the tip end 128 of the flexible body and the base region 130 that is adjacent to the wing 122. The electrically conductive contacts 126 (or "contacts") may be located inward of the flexibly body outer surface 132 and exposed by way of a corresponding plurality of contact windows (or "windows") 134 that extend through the outer surface of the flexible body to the contacts. The contacts 126 are each connected to a respective lead wire 136 that extends through the flexible body 124. In some instances, the flexible body 124 may include a depth (or "cochleostomy") marker 138 that is a predetermined distance from the tip end 128. In addition to functioning as a handle, the wing 122 provides tension relief for the lead wires 136 that do not run straight through the wing. A tubular member 140 (FIG. 3), which may consist of tubes of different sizes, extends from the wing 122 to the housing 112. The lead wires 136 extend through the tubular member to a connector (not shown) in the housing 112. The connection between the stimulation assembly 102 and the cochlear lead 104 may be a temporary connection, whereby the stimulation assembly and a cochlear lead may be disconnected from one another (e.g., for in situ replacement of the stimulation assembly), or a permanent connection.

The exemplary projections 108, which extend outwardly from the electrode array flexible body 124 and rearwardly toward the basal region 130, include a base end 142 at the flexible body and a tip end 144. The projections 108 also define an angle Θ with the adjacent portion of the flexibly body outer surface 132, which may range from about 30° to about 80° and is an acute angle of about 45° in the illustrated embodiment. As used herein, the word "about" means±10%. So oriented, the projection base end 142 of each projection 108 is closer to flexible body tip end 128 than the tip end 144 of the projection. There are three pluralities 108-1 to 108-3 of longitudinally spaced projections 108, with the projection pluralities 108-1 and 108-2 on either side of the flexible body 124 and the projection plurality 108-3 in between the projection pluralities 108-1 and 108-2 and on the side opposite the windows 134, in the illustrated embodiment. The projection pluralities 108-1 and 108-2 are offset by about 180° around the longitudinal axis LA. The number and location of the projection pluralities may be different in other implementations. By way of example, but not limitation, other implementations may include only two projection pluralities that are offset by about 180° around the longitudinal axis LA, there may be more than three projection pluralities within the 180° range, and/or the projection pluralities may be within a range that extends more than 180°, or less than 180°, around the longitudinal axis LA.

Although the present inventions are not so limited, the flexible body 124 of the exemplary electrode array 106 illustrated in FIGS. 5-8 has a non-circular shape with a flat bottom in a cross-section perpendicular to the longitudinal axis LA, which defines the length direction of the electrode array. The flexible body 124 may also be tapered, with a perimeter in a plane perpendicular to the longitudinal axis LA that is smaller at the tip end 128 than at the basal region 130. Any other suitable flexible body shape (e.g., circular or oval), with or without a flat surface, may also be employed. Suitable materials for the flexible body 124 include, but are not limited to, electrically non-conductive resilient materials such as liquid silicone rubber (LSR), high temperature vulcanization ("HTV") silicone rubbers, room temperature vulcanization ("RTV") silicone rubbers, and thermoplastic elastomers ("TPEs"). The flexible projections 108 may be molded together with, and formed from the same material as, the flexible body 124. The flexible projections 108 may, alternatively, be separately formed and thereafter secured to the flexible body 124. Here, the flexible projections 108 may be formed from the materials described above, or from materials such as bioresorbable hydrogels and non-bioresorbable hydrogels. In either case, the flexibility of the projections 108 should be such that, if necessary, the electrode array 106 may be moved in the basal direction for repositioning or removal without damage to the adjacent cochlear tissue.

Suitable materials for the contacts 122 include, but are not limited to, platinum, platinum-iridium, gold and palladium. Although the present inventions are not limited to any particular electrode configuration, the exemplary contacts 126 may be generally U-shaped and may be formed by a placing a tubular workpiece into an appropriately shaped fixture, placing the end of a lead wire 136 into the workpiece, and then applying heat and pressure to the workpiece to compress the workpiece onto the lead wire. The insulation may be removed from the portion of the lead wire within the workpiece prior to the application of heat and pressure or during the application of heat and pressure. Various examples of tubular workpieces being compressed onto lead wires are described in WO2018/031025A1 and WO2018/102695A1. The contact windows 134 extend from the outer surface 132 of the flexible body 124 to the contacts 126, thereby exposing portions of the contacts. In the exemplary implementation, the windows 134 are the same shape and expose the same portion of the associated contacts 126.

The exemplary electrode array 106 may in some instances have preset spiral shape (e.g. a helical shape) with a tight curvature (resulting from the mold shape) in an unstressed state that corresponds to the interior geometry of the cochlea. The spiral electrode array 106 may maintained in a straightened until it is inserted into the cochlea with a stylet (not shown) or an embedded shape memory polymer element (not show) that will soften and allow the flexible body to return to the pre-curved shape during implantation.

Although the contacts 126 are all the same size and the windows 134 are all the same size in the illustrated embodiment, the contacts and/or windows may be different in sizes and/or shapes in other implementations. For example, the contacts may be larger in the portion of the array that will be positioned in the basal region of the cochlea than the contacts in the portion that will be positioned in the apical region of the cochlea. The position of the contacts may be such that a portion of each contact is aligned with the flexible body outer surface, thereby eliminating the need for a window.

Figure 9:
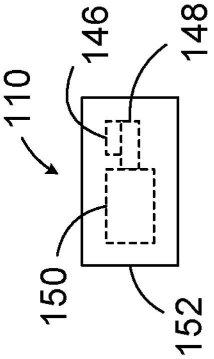
FIG. 9 is side view of an exemplary vibration device.
Figure 10:
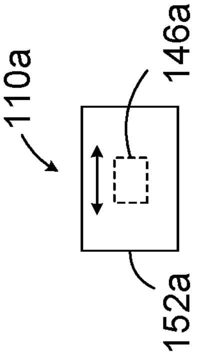
FIG. 10 is side view of an exemplary vibration device.
Figure 11:
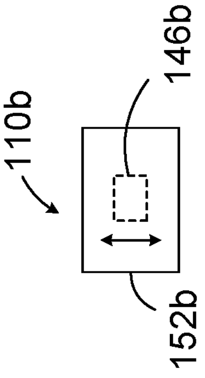
FIG. 11 is side view of an exemplary vibration device.

A wide variety of vibration devices may be employed. The exemplary vibration device 110 illustrated in FIG. 9 is a rotating out-of-balance mass vibration device which includes an out-of-balance mass 146 that is mounted on the rotating shaft 148 of a motor 150. The out-of-balance mass 146 and motor 150 may be located within a housing 152. Power for the vibration device 110 may be provided by way of wires 154 (FIGS. 6 and 7) that extend to connector 160 as is discussed below with reference to FIG. 3. The exemplary vibration device **110*a* illustrated in FIG. 10 includes a mass 146*a*, within a housing 152*a*, that vibrates in the direction of the longitudinal axis LA. Here, movement is the result of the directional dependency (or "anisotropy') of the coefficient of friction between the flexible projections 108 and the cochlear tissue. The exemplary vibration device 110*b* illustrated in FIG. 11 includes a mass 146*b*, within a housing 152*b*, that vibrates in a direction that is perpendicular to the longitudinal axis LA. Vibration in this direction results in reliable movement of the associated electrode array, despite variations in cochlear conditions and a relatively low coefficient of friction between the flexible projections 108 and the cochlear tissue. Power for the vibration devices 110*a* or 110*b* may also be provided by way of wires 154**.

Figure 13:
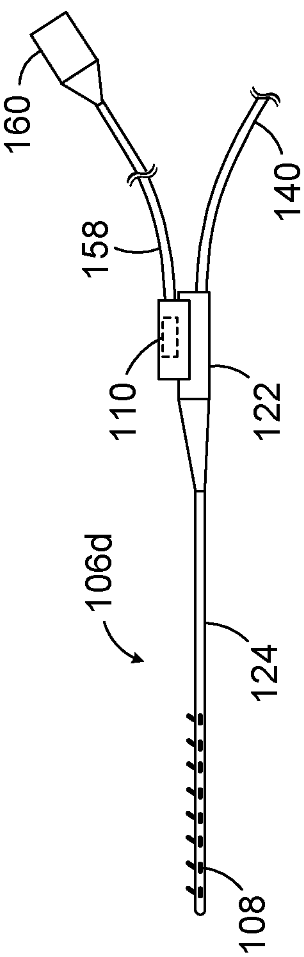
FIG. 13 is a side view of an electrode array in accordance with one embodiment of a present invention.
Figure 14:
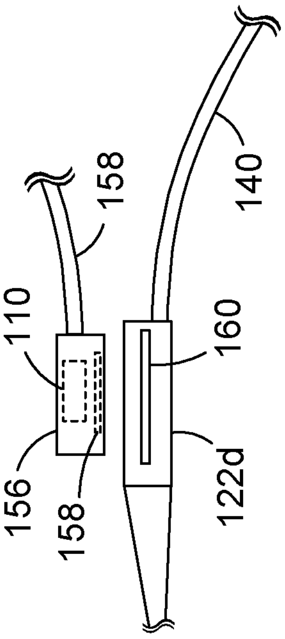
FIG. 14 is an exploded view of a portion of the electrode array illustrated in FIG. 13.

The vibration device 110 (or **110*a* or 110*b*) is located within the flexible body 124 in the exemplary electrode array 106 illustrated in FIGS. 3-8. In particular, the vibration device 110 is located within the apical region of the flexible body 124 between adjacent contacts 126. In other implementations, the vibration device 110 (or 110*a* or 110*b*) may be associated with other portions of an electrode array, either permanently or temporarily on an as-needed basis. For example, the electrode array 106*c* illustrated in FIG. 12, which is otherwise identical to electrode array 106, includes a vibration device such as vibration device 110 (or 110*a* or 110*b*) that is located within the wing 122. Turning to FIGS. 13 and 14, the exemplary electrode array 106*d* does not include a vibration device within the wing 122*d* or the flexible body 124. Instead, a selectively attachable and detachable housing 156, in which a vibration device such as vibration device 110 (or 110*a* or 110*b*) is located, may be mounted onto the wing 122*d* as necessary. Although other connector arrangements may be employed, the housing 156 includes a pair of projections 158 (one shown) and the wing 122*d* includes a corresponding pair of indentations 160 (one shown) in which the projections are located when the housing is mounted onto the wing. A selectively attachable and detachable housing with a vibration device may, alternatively, be mountable on the basal region of a flexible body 124** in other implementations.

Figure 16:
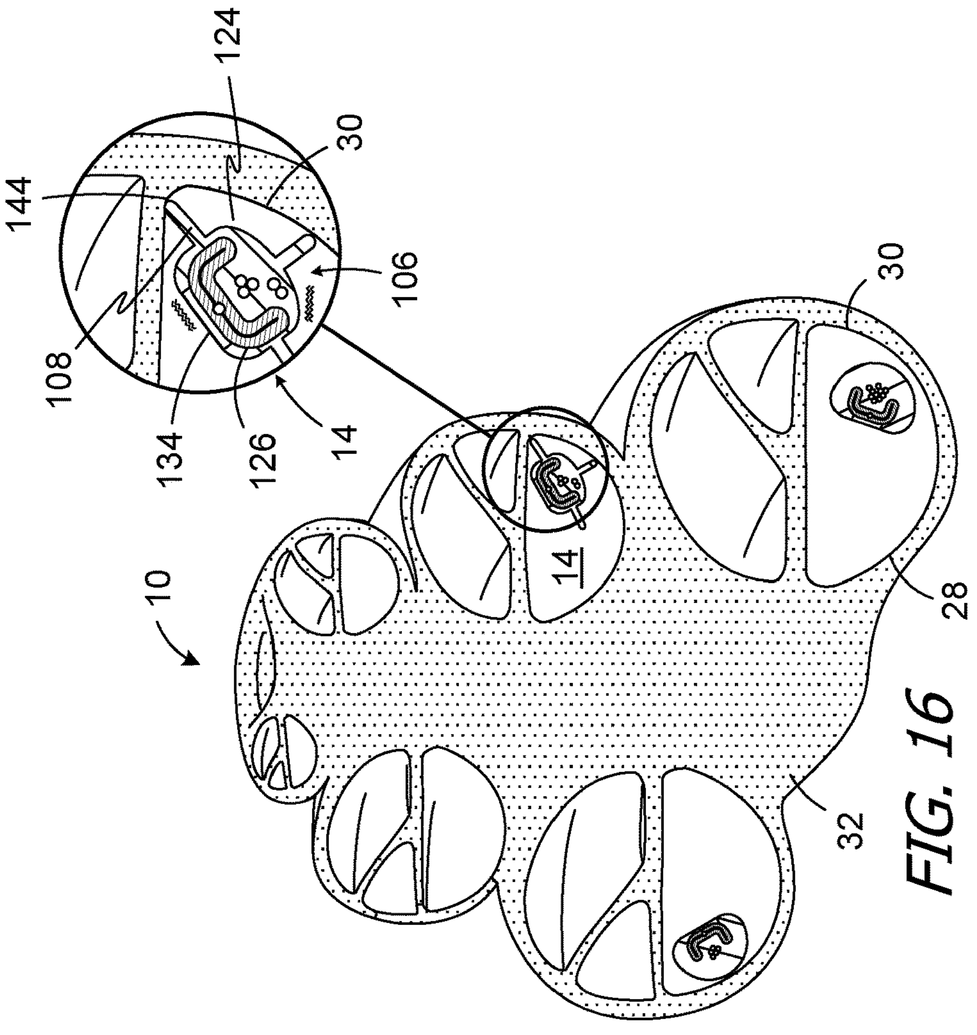
FIG. 16 is a section view of the electrode array illustrated in FIG. 3 within the cochlea in a vibrating state.
Figure 15:
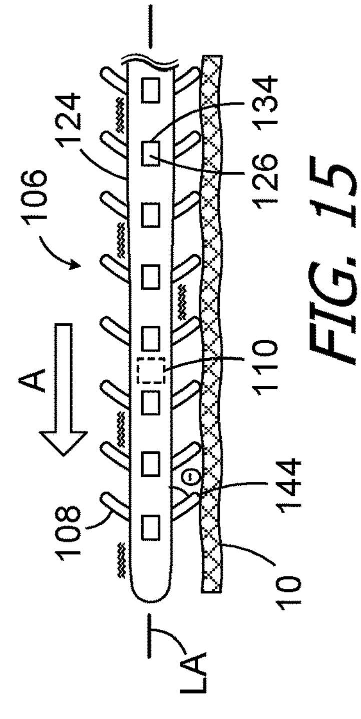
FIG. 15 is a bottom view of a portion of the electrode array illustrated in FIG. 3 in a vibrating state.

As illustrated for example in FIGS. 15 and 16, the vibration of the electrode array 106 resulting from actuation of the associated vibration device, e.g., vibration device 110, results in movement of the electrode array (as well as the remainder of the cochlear lead 104) in the apical direction represented by arrow A. In particular, while the projections 108 are in contact with cochlear tissue (e.g., a wall of the scala tympani 14) at the angle Θ and there is friction between the projection ends 144 and the cochlear tissue, actuation of the vibration device results in high-frequency whole-body oscillations of the flexible body 124. Asymmetric interactive normal forces are thereby created, which results in the generation of asymmetric frictional forces between the projection ends 144 and cochlear tissue that move the electrode array 106 in the apical direction A.

The vibration-induced movement of the above-described electrode arrays may be controlled by controlling the amplitude and frequency of the vibrations which, in turn, may be controlled by controlling power supplied to the associated vibration devices. Referring for example to FIG. 3, power may be supplied by the exemplary power supply and control device 200 which includes a housing 202, a power supply 204, a controller 206 and a touch screen or other user interface 208. The power supply and control device 200 also includes a cable 210 and a connector 212, while the exemplary lead 104 includes a tubular member 158 through which the wires 154 (FIGS. 6 and 7) extend to a corresponding connector 160. The connectors 160 and 212 may be connected as necessary, e.g., during the initial implantation of the associated cochlear lead or a subsequent repositioning, and disconnected when not in use.

The user interface 208 may be used to vary the supplied power as necessary to achieve the desired vibration of the electrode array (e.g., array 106) and the corresponding movement in the apical direction. In some instances, amplitude of the vibrations may range from 5 μm to 50 μm and frequency may range from 0 Hz to 200 Hz. For example, the speed of apical movement of the electrode array may be controlled by setting an amplitude and frequency that will produce the desired speed. The driving force in the apical direction may also be limited to a predetermined level by adjusting the amplitude and frequency. For example, the driving force may be limited to a level below which the associated electrode array will cause trauma to the cochlea. In other words, if the resistance is too great, the cochlear lead will simply stop moving. Power delivery times limits may also be set by way of the user interface 208.

Figure 12:
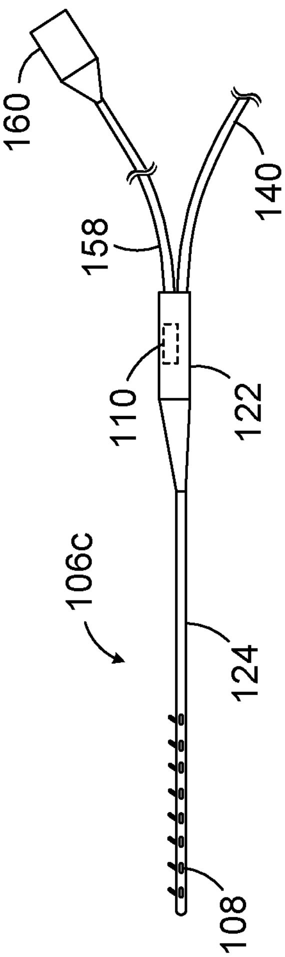
FIG. 12 is a side view of an electrode array in accordance with one embodiment of a present invention.

Turning to FIG. 12, the vibration device 110 located within the wing 122 may be also be connected to a connector 160 by way of shorter wires 154 (not shown) that extend through the tubular member 158. Similarly, as shown in FIGS. 13 and 14, the vibration device 110 withing the housing 156 may be also be connected to a connector 160 by way of shorter wires 154 (not shown) that extend through the tubular member 158.

Figure 17:
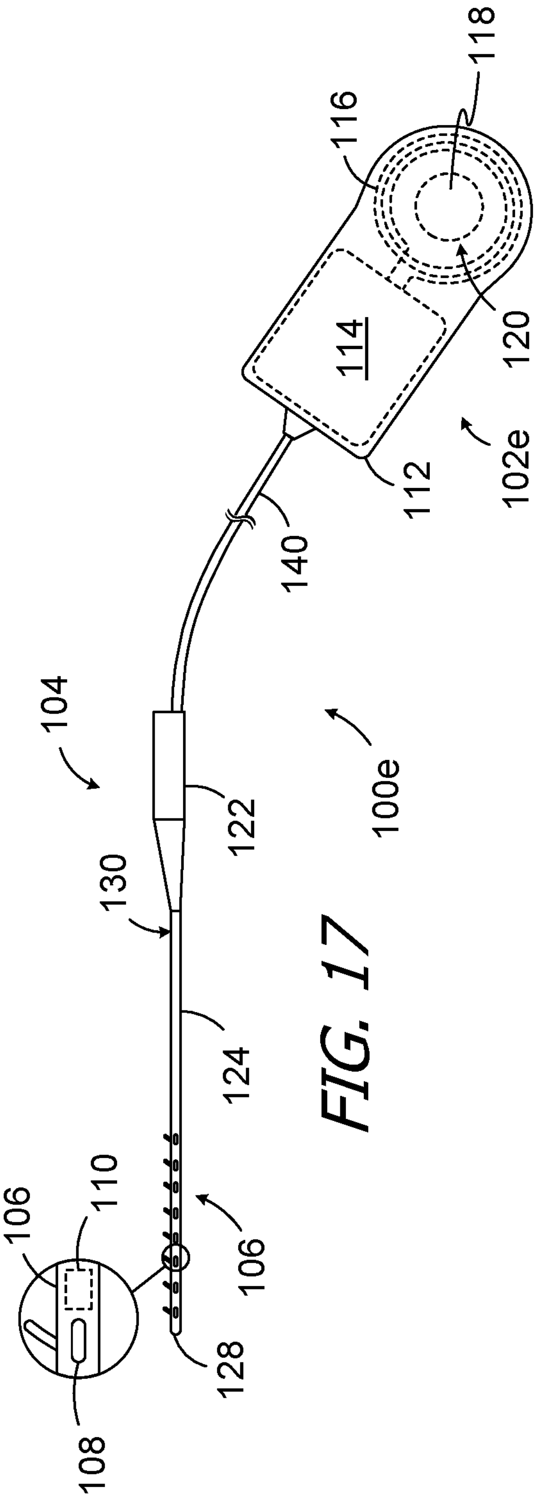
FIG. 17 is a top view of an implantable cochlear stimulator in accordance with one embodiment of a present invention.
Figure 18:
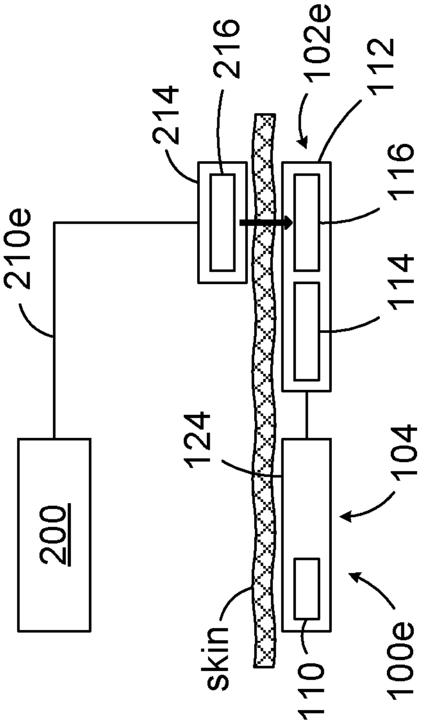
FIG. 18 is a diagrammatic view of the implantable cochlear stimulator illustrated in FIG. 17 and a vibration energy source in accordance with one embodiment of a present invention.

Power for the vibration device may be wirelessly provided in other implementations. To that end, and referring to FIGS. 17 and 18, the exemplary cochlear implant **100*e* is substantially similar to cochlear implant 100 and similar elements are represented by similar reference numerals. For example, the cochlear implant 100*e* includes a cochlear lead 104 with an electrode array 106 and a vibration device 110. Here, however, power for the exemplary vibration device 110 is wirelessly supplied by way of the antenna 116 of the stimulation assembly 102. The vibration device wires 154 (FIGS. 6 and 7) extend through the tubular member 140 along with the lead wires 136 to the stimulation assembly 102*e*. Power may be supplied and controlled by the above-described power supply and control device 200. A wireless transmitter 214 with an antenna 216 may be connected to the power supply and control device 200 with a cable 210*e*. The antenna 216 is configured to transcutaneously transmit power to the stimulation assembly antenna 116. During an insertion procedure, or a later revision procedure, power received by the antenna is transferred, by way of the processor assembly 114 and vibration device wires 154, to the vibration device 110**.

Although the inventions disclosed herein have been described in terms of the preferred embodiments above, numerous modifications and/or additions to the above-described preferred embodiments would be readily apparent to one skilled in the art. The inventions also include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A cochlear implant, comprising:

a housing;

an antenna within the housing;

a stimulation processor within the housing operably connected to the antenna; and a cochlear lead including an electrode array operably connected to the stimulation processor and including a flexible array body with a basal region and an apical region, a plurality of electrically conductive contacts on the flexible array body, and a plurality of flexible projections that extend outwardly from the flexible array body and that each include a base end and a tip end, a handle associated with the basal region of the flexible array body, a plurality of wires that are respectively connected to the plurality of electrically conductive contacts and that extend through the array body and the handle, and a vibration device that is located within the apical region of the flexible array body or is located within the handle, wherein the flexible projections are configured such that vibration of the flexible array body by the vibration device results in the generation of asymmetric frictional forces between the projection tip ends and cochlear tissue that move the flexible array body in an apical direction.

2. A cochlear implant as claimed in claim 1, wherein the vibration device is located within the flexible array body within the apical region and is located between adjacent electrically conductive contacts.

3. A cochlear implant as claimed in claim 1, wherein the flexible array body defines a longitudinal axis and an axial direction; and the vibration device is selected from the group consisting of a rotating out-of-balance mass, a mass that vibrates in the axial direction, and a mass that vibrates in a direction perpendicular to the axial direction.

4. A cochlear implant as claimed in claim 1, wherein the flexible array body defines a longitudinal axis; and the plurality of flexible projections includes first and second pluralities of flexible projections that are respectively located on opposite sides of the longitudinal axis and a plurality of flexible projections between the first and second pluralities of flexible projections.

5. A cochlear implant as claimed in claim 1, wherein at least some of the flexible projections define an acute angle with the flexible array body.

6. A cochlear implant as claimed in claim 1, wherein the flexible array body includes an apical end; and at least some of the flexible projections are oriented such that the base end of the flexible projections is closer to the apical end of the flexible array body than the tip end of the flexible projections.

7. A cochlear implant as claimed in claim 1, wherein the flexible projections are formed from the same material as the flexible array body.

8. A cochlear implant as claimed in claim 1, wherein the flexible projections are formed from different material than the flexible array body.

9. A cochlear implant as claimed in claim 1, wherein the contacts are embedded within the flexible array body; and the flexible array body includes a plurality of windows that respectively expose portions of the contacts.

10. A method, comprising:

moving a cochlear implant electrode array, including a flexible array body, a plurality of electrically conductive contacts on the flexible array body, and a plurality of flexible projections, each having a base end and a tip end, that extend outwardly from the flexible array body and the tip ends are in contact with the cochlea, in an apical direction by vibrating the flexible array body with a vibration device located within the flexible array body in such a manner that asymmetric frictional forces are created between the projection tip ends and the cochlea that move the electrode array in the apical direction.

11. A method as claimed in claim 10, wherein vibrating the flexible array body with the vibration device comprises supplying power to the vibration device.

12. A method as claimed in claim 11, further comprising: varying the amplitude and/or frequency of the vibrations.

13. A method as claimed in claim 11, wherein the cochlear implant electrode array is connected to a cochlear implant stimulation assembly; and supplying power comprises supplying power with a wireless transcutaneous connection between the cochlear implant stimulation assembly and a power supply.

14. A method as claimed in claim 11, wherein the cochlear implant electrode array is connected to a cochlear implant stimulation assembly; and supplying power comprises supplying power with a wired connection between the cochlear implant stimulation assembly and a power supply.

15. A cochlear implant, comprising:

a housing;

an antenna within the housing;

a stimulation processor within the housing operably connected to the antenna; and a cochlear lead including an electrode array operably connected to the stimulation processor and including a flexible array body, and a plurality of electrically conductive contacts on the flexible array body, a vibration device located within the flexible array body, and a plurality of flexible projections that extend outwardly from the flexible array body, that each include a base end and a tip end, and that are configured such that vibration of the flexible array body by the vibration device results in the generation of asymmetric frictional forces between the projection tip ends and cochlear tissue that move the flexible array body in an apical direction.

16. A cochlear implant as claimed in claim 15, wherein at least some of the flexible projections define an acute angle with the flexible array body.

17. A cochlear implant as claimed in claim 15, wherein the flexible array body includes a basal region and an apical region; the electrode array further includes a handle associated with the basal region; and the vibration device is located within the flexible array body within the apical region or is located within the handle.

* * * * *